United States Patent [19]
Guerrero et al.

[11] Patent Number: 5,935,584
[45] Date of Patent: Aug. 10, 1999

[54] VITAMIN C DELIVERY SYSTEM

[75] Inventors: Angel Augusto Guerrero, Huntington; Anthony Vargas, Monroe; Alan Joel Meyers, Trumbull, all of Conn.

[73] Assignee: Elizabeth Arden Company, New York, N.Y.

[21] Appl. No.: 08/181,273

[22] Filed: Jan. 13, 1994

[51] Int. Cl.$^6$ .................. A61K 7/00; A61K 7/06
[52] U.S. Cl. .................. 424/401; 424/62; 424/72; 424/71; 514/474
[58] Field of Search .................. 514/474; 424/62, 424/72, 71, 401

[56] References Cited

U.S. PATENT DOCUMENTS

| | | | |
|---|---|---|---|
| 1,535,529 | 4/1925 | Hopkins | 38/90 |
| 1,699,532 | 1/1929 | Hopkins | 222/94 |
| 3,873,713 | 3/1975 | Haas | 424/280 |
| 4,057,620 | 11/1977 | Prugnaud | 514/474 |
| 4,211,341 | 7/1980 | Weyn | 222/94 |
| 4,372,874 | 2/1983 | Modrovich | 436/176 |
| 4,487,757 | 12/1984 | Kiozpeoplou | 424/7.1 |
| 4,528,180 | 7/1985 | Schaeffer | 424/52 |
| 4,687,663 | 8/1987 | Schaeffer | 424/52 |
| 4,818,521 | 4/1989 | Tamabuchi | 424/62 |
| 4,839,161 | 6/1989 | Bowser et al. | 424/59 |
| 4,849,213 | 7/1989 | Schaeffer | 424/53 |
| 4,938,969 | 7/1990 | Schinitsfy | 514/474 |
| 4,983,382 | 1/1991 | Willmott et al. | 424/62 |
| 5,035,859 | 7/1991 | Gu | 422/28 |
| 5,078,989 | 1/1992 | Ando et al. | 424/62 |
| 5,137,723 | 8/1992 | Yamamoto et al. | 424/400 |
| 5,140,043 | 8/1992 | Darr et al. | 514/474 |
| 5,298,237 | 3/1994 | Fine | 514/474 |
| 5,308,621 | 5/1994 | Taylor | 514/474 |

FOREIGN PATENT DOCUMENTS

| | | |
|---|---|---|
| 27 44 976 | 10/1977 | Germany. |
| 929351 | 6/1963 | United Kingdom. |
| 2052986 | 2/1981 | United Kingdom. |
| WO 87/06465 | 11/1987 | WIPO. |

OTHER PUBLICATIONS

European Search Report EP 95 30 1306.

*Primary Examiner*—Sally Gardner-Lane
*Attorney, Agent, or Firm*—Milton L. Honig

[57] ABSTRACT

A cosmetic product formed as a multi-compartment dispenser is provided wherein an aqueous and an anhydrous composition are stored in separate compartments. The anhydrous composition includes ascorbic acid delivered in a pharmaceutically acceptable carrier. The aqueous composition includes an alkaline agent present to cause a rise in pH of the anhydrous composition as both compositions are blended together after being dispensed from their respective compartments.

13 Claims, No Drawings

VITAMIN C DELIVERY SYSTEM

BACKGROUND OF THE INVENTION

1. Field of the Invention

The invention relates to a cosmetic product that can stably store ascorbic acid and then deliver same to the skin.

2. The Related Art

Ascorbic acid, also known by its common name of Vitamin C, has long been recognized as an active substance benefiting skin appearance. Vitamin C reportedly increases the production of collagen in human skin tissue. Wrinkles and fine lines are thereby reduced. An overall healthier and younger-looking appearance results. Vitamin C has also found utility as an ultraviolet ray blocking or absorbing agent. Whitening or bleaching skin compositions have also employed Vitamin C utilizing its property of interference with the melanin formation process. There also is a belief that ascorbic acid interacts with the human immune system to reduce sensitivity to skin-aggravating chemicals. Reduced levels of Vitamin C concentration on the skin have also been implicated with an increase in stress. From all of the foregoing perspectives, Vitamin C or ascorbic acid may provide significant benefit when topically applied.

Unfortunately, Vitamin C is a very unstable substance. Although it is readily soluble in water, rapid oxidation occurs in aqueous media. Solubility of ascorbic acid has been reported to be relatively poor in nonaqueous media, thereby preventing an anhydrous system from achieving any significant level of active concentration.

The art has sought to overcome the problem in a variety of ways. One approach is the preparation of ascorbic acid derivatives. These derivatives have greater stability than the parent compound and, through biotransformation or chemical hydrolysis, can at the point of use be converted to the parent acid. For instance, U.S. Pat. No. 5,137,723 (Yamamoto et al) and U.S. Pat. No. 5,078,989 (Ando et al) provide glycosylate and ester derivatives, respectively.

U.S. Pat. No. 4,818,521 (Tamabuchi) describes under the background technology a so-called two-pack type cosmetic wherein Vitamin C powder and other ingredients are separately packaged in different containers with mixing just prior to use of the cosmetic. The mixing procedure and expensive packaging were said to be drawbacks of this system. The patent suggests stable oil-in-water type emulsions that are weakly acidic and wherein ascorbic acid has been premixed with a stabilizing oil.

Maintenance of pH below about 3.5 has also been suggested in U.S. Pat. No. 5,140,043 (Darr et al) as a stabilization means for aqueous compositions of ascorbic acid.

Water compatible alcohols such as propylene glycol, polypropylene glycol and glycerol have been suggested as co-carriers alongside water to improve stability. An illustration of this approach can be found in U.S. Pat. No. 4,983,382 (Wilmott and Znaiden). Therein a blend of water and water-miscible organic solvent are combined as a stabilizing system. At least about 40% of the organic solvent must be ethanol while the remainder may be selected from such alcohols as propylene glycol, glycerin, dipropylene glycol and polypropylene glycol.

U.S. Pat. No. 4,372,874 (Modrovich) has reported incorporation of relatively large amounts of ascorbic acid in a polar water-miscible organic solvent such as dimethyl sulfoxide. Levels of water are kept below 0.5% through addition of a particulate desiccant to the carrier. Although highly polar systems such as dimethyl sulfoxide may be effective, this and related carriers are toxicologically questionable.

Accordingly, it is an object of the present invention to provide a delivery system for ascorbic acid in which the compound is storage stable.

Another object of the present invention is to provide a delivery system which delivers ascorbic acid at a pH compatible with that of human skin to avoid irritation and obtain better penetration.

Still another object of the present invention is to provide a system for delivering ascorbic acid that is sufficiently transparent so as to render the system aesthetically pleasing.

A still further object of the present invention is to provide a system for delivering ascorbic acid to the skin that includes a carrier which is at least half water.

These and other objects of the present invention will become more readily apparent through the following summary, detailed discussion and Examples.

SUMMARY OF THE INVENTION

A cosmetic product is provided which is formed as a multi-compartment dispenser, wherein a first and second substance are stored apart from one another in separate compartments of the dispenser:

(i) the first substance being an anhydrous composition comprising from:
   a) from 0.001 to 50% by weight of ascorbic acid; and
   b) from 0.01 to 99% by weight of a pharmaceutically acceptable carrier; and
(ii) the second substance being an aqueous composition comprising an alkaline agent present in an effective amount to cause a rise in pH of the first substance when blended therewith.

DETAILED DESCRIPTION OF THE INVENTION

Now it has been discovered that a multi-compartment dispenser can be utilized for stably retaining under storage an anhydrous ascorbic acid-containing composition. A separate second compartment may be utilized to store an aqueous composition whose components over time would ordinarily adversely interact with the ascorbic acid to decrease the ascorbic acid activity. Especially present in the aqueous composition will be an alkaline agent capable of producing a rise in pH of the anhydrous composition when blended together just prior to use. In this manner, a relatively more alkaline final blended composition can be delivered to the skin whose acidity is insufficient to cause skin irritation but, nevertheless, delivers active ascorbic acid.

Thus, one essential element of the present invention is an anhydrous composition that includes ascorbic acid. The amount of ascorbic acid should range from about 0.001 to about 50%, preferably from about 0.01 to about 10%, optimally between about 3 and 6% by weight of the anhydrous composition.

A wide variety of vehicles or carriers can be utilized to deliver the ascorbic acid. The carrier must be inert to the active substance. Usually the carrier is an ingredient present in highest amounts and generally can range from about 5 to about 99.9%, preferably from about 25 to about 90%, optimally between about 70 and 85% by weight of the anhydrous composition.

Illustrative of the carriers for the anhydrous composition of this invention are glycerin, polyethylene glycols, polypropylene glycols, ethylene oxide/propylene oxide copolymers, alkoxylated polysaccharides, alkoxylated glycerin and monoalkyl glycol ethers.

These carriers are distinguished by their miscibility with water and having at least one free hydroxyl group. Among the preferred carriers are glycerin, glycereth-7, polyethylene glycol (M.W. 400), polyglycerols and diethylene glycol monoethyl ether. The aforementioned class of carriers has been found to stabilize ascorbic acid.

Lower alcohols such as ethyl alcohol may be present to assist the carrier. However, it is best to keep the concentration of lower alcohol at no higher than 20%, preferably ranging from 0.1 to about 10% by weight.

Esters are another category of suitable carrier. Among esters that may be utilized are:

(1) Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, isononyl isononanoate, isodecyl isononanoate, lauryl lactate, myristyl lactate, and cetyl lactate. Particularly preferred are $C_{12}$–$C_{15}$ alcohol benzoate esters.

(2) Alkenyl esters of fatty acids having 10 to 20 carbon atoms. Examples thereof include oleyl myristate, oleyl stearate, and oleyl oleate.

(3) Ether-esters such as fatty acid esters of ethoxylated fatty alcohols.

(4) Polyhydric alcohol esters. Ethylene glycol mono and di-fatty acid esters, diethylene glycol mono- and di-fatty acid esters, polyethylene glycol (200–6000) mono-and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(5) Wax esters such as beeswax, spermaceti, myristyl myristate, stearyl stearate.

(6) Sterols esters, of which cholesterol fatty acid esters are examples thereof.

Emulsifiers may also be present in the compositions of this invention. These emulsifiers may either be anionic, nonionic, cationic or amphoteric type. Nonionic emulsifiers are particularly preferred, especially polyoxyalkylene polyol fatty acid esters (which may also operate as ester emollients). Most preferred is polyethylene oxide (15) trimethylolpropane isostearate. Levels of emulsifier may range anywhere from about 0.1 to about 20%, preferably between about 1 and 5% by weight.

Silicone oils may also be used as carriers. These oils may be either volatile or nonvolatile. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Examples of preferred volatile silicone oils useful herein include: Dow Corning 344, Dow Corning 345 and Dow Corning 200 (manufactured by Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

The nonvolatile silicone oils useful in compositions of this invention are exemplified by the polyalkyl siloxanes, polyalkylaryl siloxanes and polyether siloxane copolymers. The essentially nonvolatile polyalkyl siloxanes useful herein include, for example, polydimethyl siloxanes with viscosities of from about 5 to about 100,000 centistokes at 25° C. Among the preferred nonvolatile silicones useful in the present compositions are the polydimethyl siloxanes having viscosities from about 10 to about 400 centistokes at 25° C. Such polyalkyl siloxanes include the Viscasil series (sold by General Electric Company) and the Dow Corning 200 series (sold by Dow Corning Corporation). Polyalkylaryl siloxanes include poly(methylphenyl)siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Cetyl dimethicone copolyol, cetyl dimethicone and dimethicone copolyol are especially preferred because these materials also function as emulsifiers and emollients.

Among other skin benefit agents which may be present in the anhydrous compositions of this invention are fatty acids having from 10 to 20 carbon atoms. Suitable examples of the fatty acids include pelargonic, lauric, myristic, palmitic, stearic, isostearic, hydroxystearic, oleic, linoleic, ricinoleic, arachidic, behenic, and erucic acids. These materials may be present in amounts anywhere from about 0.1 to about 20%. preferably between about 2 and 10% by weight of the anhydrous composition.

Acidifying agents may also be included in the anhydrous composition. These may be either organic or inorganic and range in amount from about 0.1 to about 20%, preferably between about 1 and 10%, optimally between about 2 and 6% by weight. The acids may include alginic acid, citric acid, malic acid, succinic acid, lactic acid, glycolic acid, tartaric acid, sorbic acid, phosphoric acid, acid phosphate salt, acid pyrophophate salt, bitartrate salt and metal acid citrate.

According to the present invention there is also required a separate second substance which is an aqueous composition containing an alkaline material for increasing pH when blended with the nonaqueous composition. The rise in pH should be at least 0.5 units, preferably at least 1.0 units and optimally at least 2 units on the pH acidity scale. Ordinarily the pH of the first substance will range from about 1 to about 4, preferably from about 2 to about 3.6. The second substance will have a pH ranging from about 7 to about 11, preferably from about 8 to about 9. When the first and second substances are combined, the blend should have a pH ranging from about 4.5 to about 6.5.

Among the most suitable alkaline materials are the bicarbonate salts, especially sodium and potassium bicarbonates. These may be present in the aqueous composition in an amount from about 1 to about 30%, preferably from about 1.5 to about 10%, optimally between about 2 and 5% by weight of the aqueous composition.

Alkaline materials stronger than bicarbonate may also be present. These include ammonia, alkylamines, hydroxyalkylamines and alkanolamines. Examples of these are triethylamine, triethanolamine, diethanolamine, tetra (hydroxypropyl) diamine, 2-amino-2-methylpropan-1-ol, 2-amino-2-ethyl-1,3-propanediol and 2-amino-2-hydroxymethyl-1,3-propanediol. Levels of the organic alkaline substance may range from about 0.1 to 10%, preferably from about 0.5 to about 5%, optimally between about 0.8 and 1.5% by weight of the aqueous composition.

As a carrier, the aqueous composition will of course include a major amount of water. This amount may range from about 40% to about 99%, preferably between about 60 and about 95%, optimally between about 80 and 85% by weight of the aqueous composition.

Supplemental carriers may include monohydric and polyhydric alcohols ranging in amounts about 1 to about 30%, especially from about 3 and 20%, optimally between about 4 and 15% by weight of the aqueous composition. Especially preferred are ethanol, isopropanol, ethylene glycol, propylene glycol and butylene glycol.

Thickeners or viscosifiers may be present in amounts up to about 10% by weight. As known to those skilled in the art, the precise amount of thickeners can vary depending upon the desired consistency and thickness of the composition. Exemplary thickeners are xanthan gum, sodium carboxymethyl cellulose, hydroxyalkyl and alkyl celluloses, and cross-linked acrylic acid polymers such as those sold by B.F. Goodrich under the Carbopol trademark. Most preferred is methyl cellulose and hydroxypropyl methyl cellulose at levels from 0.1 to 5%, preferably from about 0.2 to 1%, optimally about 0.5% by weight of the aqueous composition.

Preservatives can desirably be incorporated into the cosmetic compositions of this invention to protect against the growth of potentially harmful microorganisms. While it is in the aqueous phase that microorganisms tend to grow, microorganisms can also reside in the anhydrous or oil phase. As such, preservatives which have solubility in both water and oil are preferably employed in the present compositions. Suitable traditional preservatives for compositions of this invention are alkyl esters of parahydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methylparaben, imidazolidinyl urea, sodium dehydroacetate, propylparaben, trisodium ethylenediamine tetraacetate (EDTA) and benzyl alcohol. The preservative should be selected having regard for possible incompatibilities between the preservative and other ingredients. Preservatives are preferably employed in amounts ranging from about 0.01% to about 2% by weight of the composition.

Minor adjunct ingredients may also include fragrances, antifoam agents, opacifiers (e.g. titanium dioxide) and colorants, each in their effective amounts to accomplish their respective functions. Particularly useful minor ingredients are vitamin E linoleate, sodium hyaluronate and aloe vera gel, as well as other botanicals.

A sunscreen agent is a further desirable ingredient of the compositions of this invention. This ingredient is preferably incorporated into the aqueous composition. The term "sunscreen agent" as used herein defines ultraviolet ray-blocking compounds exhibiting absorption within the wavelength region between 290 and 400 nm. Sunscreens may be classified into five groups based upon their chemical structure: para-amino benzoates; salicylates; cinnamates; benzophenones; and miscellaneous chemicals including menthyl anthranilate and digalloyl trioleate. Inorganic sunscreens may also be used including titanium dioxide, zinc oxide, iron oxide and polymer particles such as those of polyethylene, polymethylmethacrylates and polyamides. Preferred materials include p-aminobenzoic acid and its derivatives, anthranilates; salicylates; cinnamates; coumarin derivatives; azoles; and tannic acid and its derivatives.

According to the present invention there is required a multi-compartment dispenser. Illustrative of such dispensers are those disclosed in U.S. Pat. Nos. 1,639,699 and 1,699,532, each to Hopkins, describing double collapsible tubes. Separation of reactive components is also described in U.S. Pat. No. 4,211,341 (Weyn). Other examples are those found in U.S. Pat. No. 4,487,757 (Kiozpeoplou) under FIG. 1 as well as U.S. Pat. No. 4,528,180, U.S Pat. No. 4,687,663 and U.S. Pat. No. 4,849,213, each of which is to Schaeffer.

The term "multi-compartment" may also include separation by means of encapsulation. Thus, the aqueous composition may contain microcapsules surrounding the ascorbic acid composition, the capsule walls serving as a separating compartment. Release of ascorbic acid occurs by crushing of the capsule walls as the product is rubbed onto the skin.

For purposes of this invention, the weight ratio of the aqueous to nonaqueous composition may range from about 10:1 to 1:10, preferably 2:1 to 1:2, optimally about 1:1.

The following examples will more fully illustrate the embodiments of this invention. All parts, percentages and proportions referred to herein and in the appended claims are by weight unless otherwise indicated.

EXAMPLE 1

An aqueous and an anhydrous composition were prepared according to the formulations set forth below. Each of the compositions were then charged to a respective separate compartment of a dual compartment dispensing apparatus. Each of the compositions had the following components:

COMPOSITION A

| Aqueous Composition | Wt. % |
| --- | --- |
| Deionized Water | 83.0 |
| Ethyl Alcohol | 7.5 |
| Butylene Glycol | 5.0 |
| Sodium Bicarbonate | 3.0 |
| Triethanolamine | 1.0 |
| Methocel 40-101 (Hydroxypropylmethyl cellulose) | 0.5 |

COMPOSITION B

| Anhydrous Composition | Wt. % |
| --- | --- |
| Carbowax 400 (polyethylene glycol) | 84.0 |
| Ascorbic Acid (Vitamin C) | 5.0 |
| Ethyl Alcohol | 5.0 |
| Anhydrous Citric Acid | 3.0 |
| Isostearic Acid | 3.0 |

EXAMPLE 2

An aqueous and an anhydrous composition according to the present invention are set forth below. Each of the compositions is charged to a respective separate compartment of a dual-compartment dispensing apparatus. The compositions include the following components:

COMPOSITION A

| Aqueous Composition | Wt. % |
| --- | --- |
| Deionized Water | 77.0 |
| Ethyl Alcohol | 8.0 |
| Butylene Glycol | 6.0 |
| Triethanolamine | 4.0 |
| Dimethicone Copolyol | 4.0 |
| Eusolex 232 (sunscreen) | 0.5 |
| Methyl Cellulose | 0.5 |

COMPOSITION B

| Anhydrous Composition | Wt. % |
| --- | --- |
| Glycerin | 82.0 |
| Ascorbic Acid (Vitamin C) | 5.0 |
| Ethyl Alcohol | 5.0 |
| Anhydrous Glycolic Acid | 3.0 |
| Isostearic Acid | 3.0 |
| Dimethicone | 2.0 |

EXAMPLE 3

An aqueous and an anhydrous composition according to the present invention are set forth below. Each of the compositions is charged to a respective separate compartment of a dual-compartment dispensing apparatus. The compositions include the following components:

COMPOSITION A

| Aqueous Composition | Wt. % |
| --- | --- |
| Deionized Water | 83.7 |
| Propylene Glycol | 8.0 |
| Isopropanol | 3.0 |
| 2-Amino-2-methylpropan-1-ol | 3.0 |
| Dimethicone Copolyol | 2.0 |
| Hydroxypropyl Methyl Cellulose | 0.3 |

COMPOSITION B

| Anhydrous Composition | Wt. % |
| --- | --- |
| Glycereth-7 | 83.0 |
| Ascorbic Acid (Vitamin C) | 5.0 |
| Glycerin | 5.0 |
| Anhydrous Lactic Acid | 3.0 |
| Linolenic Acid | 2.0 |
| Dimethicone Copolyol | 2.0 |

EXAMPLE 4

An aqueous and an anhydrous composition according to the present invention is set forth below. Each of the compositions is charged to a respective separate compartment of a dual-compartment dispensing apparatus. The compositions include the following components:

COMPOSITION A

| Aqueous Composition | Wt. % |
| --- | --- |
| Deionized Water | 80.7 |
| Propylene Glycol | 8.0 |
| Ethyl Alcohol | 6.5 |
| Triethanolamine | 4.0 |
| Eusolex 232 (sunscreen) | 0.5 |
| Sodium Carboxymethyl Cellulose | 0.3 |

COMPOSITION B

| Anhydrous Composition | Wt. % |
| --- | --- |
| Diethylene Glycol Monoethyl Ether | 76.0 |
| Ascorbic Acid (Vitamin C) | 10.0 |
| Ethyl Alcohol | 5.0 |
| Anhydrous Malic Acid | 3.0 |
| Oleic Acid | 3.0 |
| Polyoxyethylene 15 Trimethylolpropane Isostearate | 3.0 |

EXAMPLE 5

An aqueous and an anhydrous composition according to the present invention are set forth below. Each of the compositions is charged to a respective separate compartment of a dual-compartment dispensing apparatus. The compositions include the following components:

COMPOSITION A

| Aqueous Composition | Wt. % |
| --- | --- |
| Deionized Water | 83.0 |
| Ethyl Alcohol | 5.0 |
| Butylene Glycol | 5.0 |
| Ammonium Hydroxide | 4.0 |
| Dimethicone Copolyol | 2.5 |
| Methyl Cellulose | 0.5 |

COMPOSITION B

| Anhydrous Composition | Wt. % |
| --- | --- |
| Carbowax 400 | 80.9 |
| Isostearic Acid | 7.0 |
| Ascorbic Acid (Vitamin C) | 5.0 |
| Ethyl Alcohol | 5.0 |
| Polyoxyethylene 15 Trimethylolpropane Isostearate | 2.0 |
| Anhydrous Citric Acid | 0.1 |

The foregoing description and examples illustrate selected embodiments of the present invention and in light thereof variations and modifications will be suggested to one skilled in the art, all of which are in the spirit and purview of this invention.

What is claimed is:

1. A cosmetic product which is formed as a multi-compartment dispenser, wherein a first and second substance are stored apart from one another in separate compartments of the dispenser:
   (i) the first substance being an anhydrous composition comprising:
      a) from 0.001 to 50% by weight of ascorbic acid; and
      b) from 5 to 99.9% by weight of a pharmaceutically acceptable carrier; and (ii) the second substance being an aqueous composition with a pH ranging from about 7 to about 11 comprising from 40 to 99% water and 1 to 30% of an alkaline agent present in an effective amount to cause a rise of at least 0.5 units in pH of the first substance when blended therewith, and wherein the first and second substances are blended together just prior to use so as to topically deliver a final blended composition to skin whose acidity is insufficient to cause skin irritation but, nevertheless, delivers active ascorbic acid.

2. The cosmetic product according to claim 1 wherein the ascorbic acid is present in an amount from about 1 to about 10% by weight of the first substance.

3. The cosmetic product according to claim 1 wherein the anhydrous composition further comprises an acidifying agent present in an amount from about 0.1 to about 20% by weight thereof.

4. The cosmetic product according to claim 1 wherein the carrier is selected from the group consisting of glycerin, polyethylene glycol, polypropylene glycol, ethylene oxide/propylene oxide copolymers, alkoxylated polysaccharides, alkoxylated glycerol, monoalkyl glycol ether and mixtures thereof.

5. The cosmetic product according to claim 1 wherein the second substance includes from 1 to 30% of a solvent selected from the group consisting of monohydric and polyhydric alcohols.

6. The cosmetic product according to claim 1 wherein the aqueous composition comprises an alkaline agent which is a bicarbonate salt.

7. The cosmetic product according to claim 1 wherein the aqueous composition comprises an alkaline agent selected from the group consisting of ammonia, alkylamine, hydroxyalkylamine and alkanolamine.

8. The cosmetic product according to claim 1 wherein the aqueous composition comprises from about 60 to about 95% water by weight thereof.

9. The cosmetic product according to claim 1 wherein the rise in pH is at least 2 units.

10. A cosmetic product according to claim 1 further comprising a sunscreen agent present in an effective amount to block ultraviolet rays.

11. A cosmetic product according to claim 1 wherein the first substance has a pH ranging from about 1 to about 4.

12. A method to provide skin with an overall healthier and younger-looking appearance comprising:

providing a cosmetic product which is formed as a multi-compartment dispenser, wherein a first and second substance is stored apart from one another in separate compartments of the dispenser:

(i) the first substance being an anhydrous composition comprising:
   (a) from 0.001 to 50% by weight of ascorbic acid;
   (b) from 5 to 99.9% by weight of a pharmaceutically acceptable carrier; and (ii) the second substance being an aqueous composition with a pH ranging from about 7 to about 11 comprising from 40 to 99% water and 1 to 30% of an alkaline agent present in an effective amount to cause a rise of at least 0.5 units in pH of the first substance when blended therewith;

blending the first and second substances together just prior to use; and topically delivering the blended composition to skin, the blended composition having an acidity insufficient to cause skin irritation but, nevertheless delivering active ascorbic acid.

13. A method according to claim 12 wherein the first substance has a pH ranging from about 1 to about 4.

* * * * *

UNITED STATES PATENT AND TRADEMARK OFFICE
CERTIFICATE OF CORRECTION

PATENT NO. : 5,935,584
DATED : August 10, 1999
INVENTOR(S) : Guerrero et al.

It is certified that error appears in the above-indentified patent and that said Letters Patent is hereby corrected as shown below:

On title page item [73], change "Elizabeth Arden Company,"

to read -- Elizabeth Arden Company, Division of Conopco, Inc. --

Signed and Sealed this

Twenty-ninth Day of February, 2000

Attest:

Q. TODD DICKINSON

*Attesting Officer*        *Commissioner of Patents and Trademarks*